United States Patent [19]

Egolf

[11] Patent Number: 4,909,788
[45] Date of Patent: Mar. 20, 1990

[54] SYRINGE WITH ADJUSTABLE WINGED COLLAR

[76] Inventor: Georges Egolf, 1933 Prospect St., Sherbrooke, Canada, J1J 4C9

[21] Appl. No.: 284,294

[22] Filed: Dec. 14, 1988

[51] Int. Cl.⁴ ............................................... A61M 5/00
[52] U.S. Cl. ..................................... 604/187; 604/227
[58] Field of Search ........................ 604/187, 227, 218

[56] References Cited

U.S. PATENT DOCUMENTS

| 1,712,084 | 5/1979 | Kulik | 604/227 |
| 4,068,661 | 1/1978 | Hennings | 604/227 |

FOREIGN PATENT DOCUMENTS

| 773091 | 10/1971 | Belgium | 604/227 |
| 1059151 | 6/1959 | Fed. Rep. of Germany | 604/227 |

*Primary Examiner*—John D. Yasko
*Attorney, Agent, or Firm*—Pierre Lesperance

[57] ABSTRACT

A conventional hypodermic syringe comprises a cylindrical body with an axial funnel section at one end and an open mouth with lateral fixed wings at its other end, a piston slidably engaged through its mouth and into the main body, and a needle frictionally secured to the funnel section via a socket connector. The needle defines a bevelled free end. For proper handling of the syringe when piercing the patient's skin the bevel plane of the needle must be parallel to the longitudinal axis of the wings with the needle bevel facing away from the skin. In the present invention, the wings are not fixed to the body but an adjustable winged collar is rotatably mounted by friction fit about the mouth through an inner face thicknesswise groove engaged by an outturned flange from the mouth, wherein the collar may rotate 360° but with some level of frictional resistance. By rotatably adjusting de visu the orientation of the collar wings relative to the orientation of the bevel plane of the needle tip, instead of rotating the needle itself, the nurse does not have to touch the needle.

3 Claims, 1 Drawing Sheet

SYRINGE WITH ADJUSTABLE WINGED COLLAR

FIELD OF THE INVENTION

This invention relates to the field of medical accessories, especially hypodermic syringes.

BACKGROUND OF THE INVENTION

In the medical field, a constant preoccupation is to completely prevent any form of contamination of syringe needles, before use. Usually, when a nurse even barely accidentally touches the syringe needle before use, the whole needle must be discarded, hence a cost inefficiency. The number of such accidental contamination occurrences should not be underestimated. Why is that so? This has to do with the way the needle is mounted to the syringe cylindrical body.

Indeed, conventional syringes of the disposable type come in two parts, namely a main transparent cylindrical body, having a small conical spout at one end and a large mouth bounded by a pair of fixed wings at the other end. Such a syringe is used with a needle having a bevelled tip at one end and a socket connector at the other end and inserted in a protective rigid cylindrical sheath whereby the socket connector partially engages therein. The syringe and the needle and sheath combination are both previously sterilized and enclosed in separate sealed pouches. When the nurse has to connect the needle to the cylindrical body of the syringe, she needs to follow the following steps:

(a) open the pouches
(b) take the sheath with one hand and axially engage the projecting socket connector of the needle onto the small conical end spout of the syringe cylindrical body;
(c) remove the protective sheath from its needle;
(d) note the orientation of the bevel of the needle tip with respect to the orientation of the fixed wings;
(e) replace the protective sheath on the needle;
(f) rotate the sheath and needle combination to a fraction of a turn, empirically in order to bring the needle bevel approximately parallel to the longitudinal axis of the wings;
(g) again remove the protective sheath to verify the closeness of match between the orientation of the needle bevel with the orientation of the fixed wings;
(h) repeat steps (e) to (g) until satisfactory match of the relative orientation of the needle bevel with that of the fixed wings is established.

Such match between the orientation of the needle bevel and that of the fixed wings is a standard procedure that provides a major improvement in the skin- and blood vessel membrane-piercing capability of the needle, as is very well known in the field.

It is easy to understand that such a method is inefficient: loss of time, stress sustained by the nurse, but most importantly the possibility that the nurse will touch with one finger the needle during the replacing of the protective sheath thereon, whereas the needle must then be spent and replaced by a new one. Hence, a relatively high financial outlay based on informal statistics gathered by the present inventor. Also a lot of unnecessary movements by the nurse.

OBJECT OF THE INVENTION

The object of the invention is to increase the efficiency of nurses and other medical and paramedical staff, by correcting the above-noted deficiencies in the operation of hypodermic syringes.

SUMMARY OF THE INVENTION

In accordance with the object of the invention, the present invention is directed to correct the above-described problem by, instead of rotating the needle/sheath relative to the syringe wings, rather rotating the syringe wings relative to the needle sheath, wherein absolutely no contact with the needle is necessary, and wherein the match between the orientation of the needle bevel and that of the syringe wings is effected in a single pass.

More specifically, the present invention relates to a hypodermic syringe comprising: a cylindrical body with a nozzle section at one end and an open mouth at its other end, and characterized in that there is further included a collar member, rotatably mounted about said mouth, guide means, to maintain said collar member in register with said mouth during the rotation thereof, friction means, to prevent rotation of said collar member up to a threshold rotating force beyond which said collar will rotate, and opposite wings fixed to said collar member.

Preferably, the shape of each wing of said collar member, is chosen from the group including lozenge and double-trapezoid shapes.

Advantageously, said guide means consists of an out-turned annular flange, made at the circular free end of said cylindrical body, and an annular groove, made thicknesswisely of the inner face of said collar member, said flange and groove being of mating shapes so as to be slidingly releasably engaged into each other; said friction means being defined by the interplay of said flange and groove.

Profitably, said collar member, said collar member more particularly defines a short cylindrical collar body and said wings are outwardly bent so as to be outwardly offset from said collar body relative to said mouth.

It is envisioned that at least two opposite notches be made into said cylindrical body annular flange, said notches defining means for temporarily decreasing the total diameter of said mouth for facilitating the releasable engagement/disengagement of said collar member about said mouth.

DETAILED DESCRIPTION OF THE INVENTION

Figure 1:
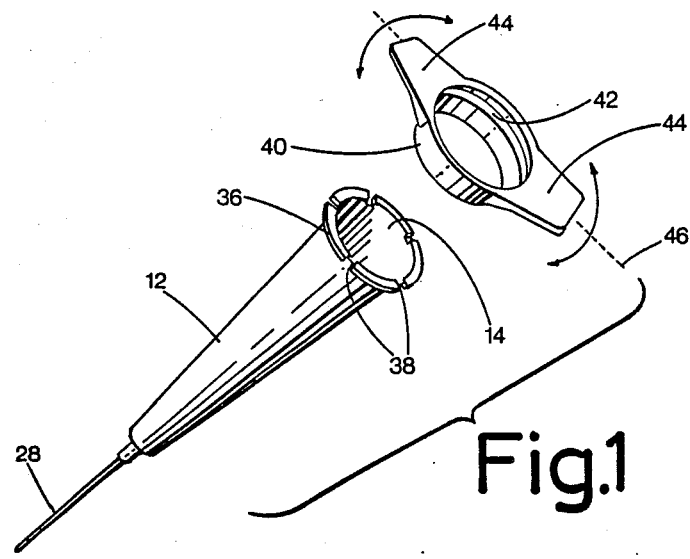
FIG. 1 is an axonometric view of a syringe body, made in accordance with the teachings of the invention, showing the winged collar removed from the body thereof, a needle being secured to the syringe body.

Syringe 10 conventionally consists of a main cylindrical body 12 having an open mouth 14 at one end and a steeply conical narrowed section 16 at the opposite end. A piston 18 is engageable into main syringe body 12, defining an elastomeric plug 20 at one end and an enlarged annular head 22 at the opposite end, plug 20 and piston 18 being slidingly insertable into cylinder 12. A short, diametrically small, slightly conical nozzle 24 is integrally mounted to conical end 16, for engagement by the connecting end socket 26 of an elongated hypodermic needle 28. Needle 28 has a bevelled free end 30 designed to facilitate the piercing of living tissues. Bevelled tip 30 defines a bevel plane 32 making a small angle $\theta$ generally of about 20° to 30° with respect to the longitudinal axis of cylinder body 12.

In accordance with the invention, the end of body 12 opposite nozzle 24, i.e. about mouth 14, is provided with an integral annular outturned flange 36. Flange 36 includes a few spaced square notches 38, e.g. five equally spaced notches 38 as illustrated in FIG. 1. A free collar 40 of circular shape and of semi-rigid construction is releasably engaged around mouth 14, and includes an annular central groove 42 made thicknesswisely of its inner face for accommodating said flange 36 of the cylinder body 12. Collar 40 is provided with opposite, integral wings 44, 44, and is engaged in position around mouth 14 by being first engaged around the nozzle carrying end of body 12 and thereafter slid over the length of cylinder body 12 up to the level of mouth 14. Collar 40 engages flange 36 by friction fit, in a snap action.

The width of annular flange 36 should be at least twice the thickness of body 12, wherein its total diameter may be larger by for example 300° relative to the total (exterior) of the body 12.

Notches 38 constitute weak parts fo the flange 36, which will provide some radial flexibility thereof (i.e. which will permit temporary reduction in diameter of the flange 36 under forcible action thereabout) for enabling engagement of collar 40 therearound.

The two opposite integral wings 44, are thicknesswisely and widthwisely tapering radial extensions of the collar 40. When seen in plan view, the wings 44 define a double trapezoidal shape having a longitudinal axis 46 as shown in FIG. 1. Wings 44 are slightly inclined away from nozzle 24 to facilitate the manipulation of the syringe.

When collar 40 is mounted around mouth 14, the semi-rigid construction of the collar enables 360° rotation thereof around mouth 14 upon forcible action being applied thereto, yet will normally retain its relative orientation when no forcible action is applied. That is to say, when the nurse holds body 12 with one hand and uses her thumb and forefinger from the other hand to rotate collar 40 (see the arrows in FIG. 1), by maneuvering the two wings 44, she will feel a frictional resistance wherein she will have to use a relatively high level of pivotal motion of her two fingers before relative rotation of the collar will be possible.

Figure 2:
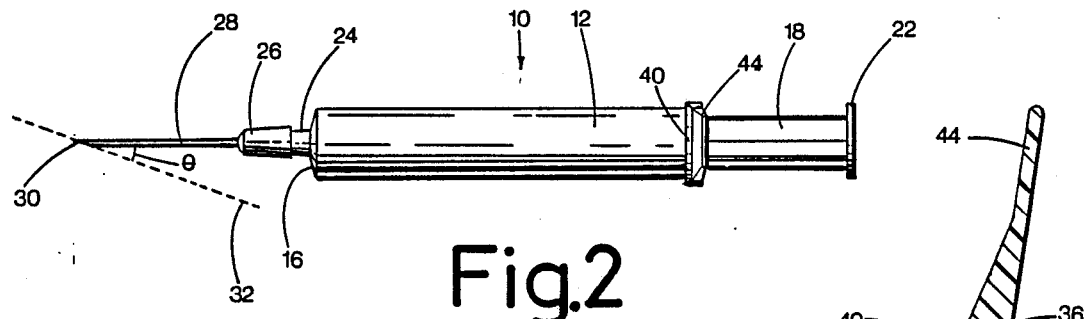
FIG. 2 is a plan view of the complete syringe including its piston and of a needle secured in properly oriented position.
Figure 4:
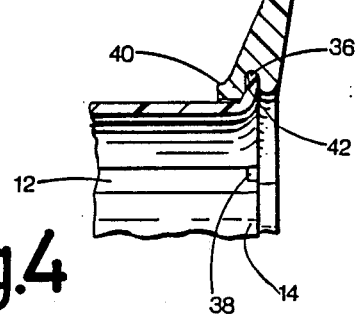
FIG. 4 is an enlarged partially sectional view of the syringe body and winged collar.
Figure 3:
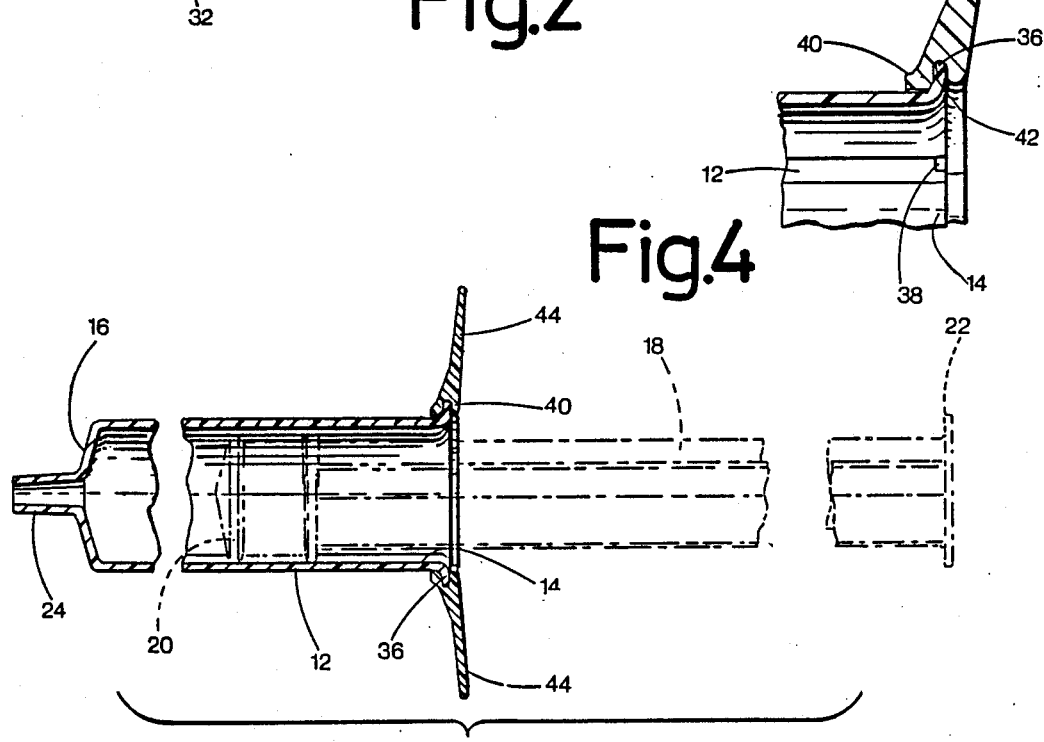
FIG. 3 is an enlarged sectional view of the syringe body, including the winged collar, and showing the piston in phantom lines.

Once the needle 28 is fitted to nozzle 24 and the needle sheath removed, it is a simple matter for the nurse to rotate wings 44 so as to bring their longitudinal axis 46 parallel to the bevel plane 32 of needle tip 30 as shown in FIG. 2. Thus, there is no need to manipulate the needle 28 before skin penetration by the needle, which often happened with conventional disposable syringes when the nurse had to rotate socket 26 for proper alignment of the bevel 30 with the fixed syringe cylinder body wings thereof. Of course, hand contact of socket 26 or needle 28 is highly undesirable, since the needle may very well have become contaminated, a health hazard to the patient.

Once the wings 44 are properly oriented relative to the needle bevel plane 32, the nurse uses wings 44, 44 and piston head 22 as finger abutting and guiding surfaces so as to orientate the bevel plane 32 away from the patient's and allowing a minimum inclination of the syringe relative to the patient's skin to achieve optimum skin piercing. During the skin-piercing step, the collar 44 will not rotate because of the frictional resistance of flange 36 within groove 42. Thus, the proper orientation of needle 28 when the epiderm is pierced will be maintained throughout the piercing, from the epiderm to and through the blood vessel membrane.

The present invention may be made part of other types of syringes such as non-disposable syringes, with little modification. More particularly, the present invention is envisioned to complete U.S. Pat. No. 4,744,741 issued May 17, 1988 in the name of the present inventor, and entitled "Syringe with automatic piston retraction".

The preferred material for body 12 including wings 44 is a translucent plastic material. However, other suitable materials can be envisioned, including metallic alloys, glass, or a plastic and metallic combination.

I claim:

1. A one-use hypodermic syringe comprising: a molded cylindrical body made of synthetic resin with a nozzle section at one end and an open mouth at its other end, an outturned annular flange formed at said other end, a collar member having an internal surface provided with an annular groove, said flange and groove being of mating shapes so as to be slidingly releasably engaged into each other with a friction fit to prevent rotation of said collar member up to a threshold rotating force beyond which said collar member will rotate, and diametrically opposite wings integral with and laterally protruding from said collar member and serving as a finger rest, said nozzle section adapted to be fitted within the socket connector of a hypodermic needle having a bevelled piercing end the bevel of which extends through a bevel plane making an acute angle with the longitudinal axis of said needle, said collar member rotatably adjustable relative to said cylindrical body so that the longitudinal axis of said wings can be brought generally parallel to said bevel plane.

2. A hypodermic syringe as defined in claim 1, further including at least two opposite notches in said cylindrical body annular flange, said notches defining means for temporarily decreasing the external diameter of said flange for facilitating the releasable engagement of said collar member with said flange.

3. A one-use hypodermic syringe as defined in claim 1 wherein said flange has an outer edge which is cross-sectionally rounded.

* * * * *